US009140707B2

(12) United States Patent
Kang et al.

(10) Patent No.: US 9,140,707 B2
(45) Date of Patent: Sep. 22, 2015

(54) SENSORS AND METHODS FOR DETECTING DISEASES CAUSED BY A SINGLE POINT MUTATION

(75) Inventors: Kyung Aih Kang, Louisville, KY (US); Stephen Peiper, Philadelphia, PA (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 1708 days.

(21) Appl. No.: 11/891,452

(22) Filed: Aug. 10, 2007

(65) Prior Publication Data

US 2009/0042210 A1    Feb. 12, 2009

(51) Int. Cl.
    *G01N 33/68*     (2006.01)
    *G01N 33/86*     (2006.01)
    *G01N 33/552*     (2006.01)
    *C07K 16/36*     (2006.01)
    *B01L 3/00*     (2006.01)

(52) U.S. Cl.
    CPC ...... *G01N 33/6878* (2013.01); *B01L 3/502715* (2013.01); *C07K 16/36* (2013.01); *G01N 33/86* (2013.01); *C07K 2317/33* (2013.01); *G01N 2333/7456* (2013.01); *G01N 2800/224* (2013.01)

(58) Field of Classification Search
    CPC ............... C07K 16/36; C07K 2317/33; G01N 33/6878; G01N 33/86; G01N 2333/7456; G01N 2800/224; B01L 3/502715
    USPC .................. 435/7.1, 7.94, 69.3, 288.5, 288.7, 435/70.21, 452, 337, 287.2, 287.9, 288.4; 436/518, 527, 531, 815, 543, 548, 69, 436/164, 165, 166, 172, 807; 530/387.9, 530/388.25, 389.3, 391.1, 391.3, 830; 422/400, 401, 405, 417, 425, 82.05, 422/82.07, 82.08, 82.11, 502
See application file for complete search history.

(56) References Cited

U.S. PATENT DOCUMENTS

| | | | |
|---|---|---|---|
| 4,622,291 A | 11/1986 | Picciolo et al. | |
| 5,316,909 A | 5/1994 | Xu | |
| 5,373,093 A | 12/1994 | Vallarino et al. | |
| 5,538,857 A | 7/1996 | Rosenthal et al. | |
| 5,726,026 A | 3/1998 | Wilding et al. | |
| 6,200,762 B1 | 3/2001 | Zlokarnik et al. | |
| 6,812,339 B1 * | 11/2004 | Venter et al. | 536/24.31 |
| 7,358,347 B1 * | 4/2008 | Chandrasekharappa et al. | 536/23.1 |
| 2003/0119070 A1 * | 6/2003 | Schaeffer et al. | 435/7.2 |
| 2009/0030655 A1 * | 1/2009 | Lewin et al. | 702/196 |

FOREIGN PATENT DOCUMENTS

WO     WO 2004/046100     6/2004

OTHER PUBLICATIONS

Ren et al., Biosensor for Diagnosing Factor V Leiden, a single amino acid mutated abnormality of Factor V, presented Aug. 2006 at the 34th Annual Conference of the International Society on Oxygen Transport to Tissue (ISOTT), Louisville, KY, and published in Adv. Exp. Med. Biol. 614: 245-252, 2008.*
Ren et al., Quantification of Fv and FvI in plasma using fiber-optic sensing system, presented Nov. 2006 at AICHE 2006 Annual Meeting, San Francisco, CA, and published at aiche.confex.com/aiche/2006/techprogram as Abstract #657a .....*
Tang et al., 2005. Preliminary study of simultaneous multi-anticoagulant deficiency diagnosis by fiber optic multi-analyte biosensor. Adv. Exp. Biol. Med. 566: 303-309.*
Jenny et al., 1987. Complete cDNA and derived amino acid sequence of human factor V. Proc. Natl. Acad. Sci. USA 84: 4846-4850.*
Bertina et al., 1994. Mutation in blood coagulation factor V associated with resistance to activated protein C. Nature 369: 64-67.*
Fare et al., 1996. Cross-reactivity analysis using a four-parameter model applied to environmental immunoassays. Bull. Environ. Contam. Toxicol. 57: 367-374.*
George P., et al., "Improved fluoroimmunoassays using the dye Alexa Fluor 647 with the RAPTOR, a fiber optic biosensor", Journal of Immunological Methods 271 (2002) 17-24.
Balcer, H., Kwon, H., Kang, K., "Assay Procedure Optimization of a Rapid, Reusable Protein C Immunosensor for Physiological Samples", Annals of Biomedical Engineering, 30, pp. 141-147, 2002.
Balcer, H., Spiker, J., Kang, K., "Effect of Blocking Buffers and Plasma Proteins on the Protein C Biosensor Performance", Proceeding of the 1999 Annual ISOTT Meeting, Oxygen Transport to Tissue XXIV, 2003.
Balcer, H., Spiker, J., Kang, K., "Sensitivity of a Protein C Immunosensor with and without Human Serum Albumin", Advances in Experimental Medicine and Biology, 471, pp. 605-612 (1999).

(Continued)

*Primary Examiner* — Gail R Gabel
*Assistant Examiner* — James L Grun
(74) *Attorney, Agent, or Firm* — Greer, Burns & Crain, Ltd.

(57) ABSTRACT

A method for generating antibodies preferable to either a normal protein and a mutated form of the normal protein, respectively, where a mutation associated with the mutated form includes either a single point mutation or a small number of point mutations where the method includes creating first and second antigenic peptides of a predetermined length corresponding respectively to common regions of the normal target protein and the mutated form, where the common regions are identical to one another except for the point mutation of the mutated form, obtaining first and second antibodies by multiplying the first and second antigenic peptides via hybridoma methods, and identifying the respective affinities of the first and second antibodies for the normal target protein and the mutated form. Also included are methods of using the first and second antibodies to detect and quantify respective amounts of a normal target protein and a mutated form of the target protein. Also included are immunological sensors the include the first and second antibodies for determining the presence and quantity of normal target proteins and mutant forms of the normal target proteins.

7 Claims, 7 Drawing Sheets

(56) References Cited

OTHER PUBLICATIONS

Berlier, J.E., Rothe, A., Buller, G., Bradford, J., Gray, D. R., Filanoski, B. J., Telford, W., G., Yue, S., Liu, J., Cheung, C.-Y., Chang, W., Hirsch, J. D. , Joseph M Beechem, J. M., Haugland, R. P., Haugland, R. P. 2003. "Quantitative Comparison of Long-wavelength Alexa Fluor Dyes to Cy Dyes: Fluorescence of the Dyes and Their Bioconjugates", J. Histochem. Cytochem., 51: 1699-1712.

Bhatia, S., Shriver-Lake, L., Prior, K., Georger, J., Calvert, J., Bredehorst, R., Ligler, F., "Use of Thiol-Terminal Silanes and Heterobifunctional Crosslinkers for Immobilization of Antibodies on Silica Surfaces", Anal. Biochem, 178, pp. 408-413, 1989.

Bouhelier, A., Renger, J., Berversluis, M., Novotny, L., "Plasmon Coupled Tip-enhanced Near-field Microscopy", Journal of Microscopy, 210: 220-224, 2003.

Buschmann, Volker, et al., "Spectroscopic Study and Evaluation of Red-Absorbing Fluorescent Dyes", Bioconjugate Chem. 2003, 14, 195-204.

Dahlback, B., "Human Coagulation Factor V Purification and Thromin-Catalyzed Activation", J. Clin. Invest., 66, pp. 583-591 (1980).

De, Swati, et al., "Enhanced fluorescence of triphenylmethane dyes in aqueous surfactant solutions at supramicellar concentrations-effect of added electrolyte", Spectrochimica Acta Part A 59 (2002) 2547-25555.

Du, Xinzhen, et al., "Comparitive study on fluorescence enhancement and quenching of europium and terbium chelate anions in cationic micelles", Spectrochimica Acta Part A 59 (2003) 271-277.

Dubertret, B., Calame, M., Libchaber, A., "Single-Mismatch Detection Using Gold-quenched Fluorescent Oligonucleotides", Nature Biotechnology, 19, pp. 365-370, 2001.

Hong, Bin, and Kyung A. Kang, "Biocompatible, nanogold-particle fluorescence enhancer for fluorophore mediated, optical immunosensor", Biosensors and Bioelectronics (2005).

Kang, K., Ryu, D., Drohan, W., Orthner, C., "Effect of Matrices on Affinity Purification of Protein C", Biotechnol Bioeng., 39, pp. 1086-1096 (1992).

Katzmann, J., Nesheim, M., Hibbard, L., Maim, K., "Isolation of Functional Human Coagulation Factor V by Using a Hybridoma Antibody", Proc. Natl. Acad. Sci. USA, 78, pp. 162-166 (1981).

Krenn, Joachim R., "Nanoparticle waveguides: Watching energy transfer", Nature Materials 2: 210-211, 2003.

Kwon, H., Balcer, H., Kankg, K., "Sensing Performance of Protein C Immuno-Biosensor for Biological Samples and Sensor Minimization", Comparative Biochemistry and Physiology Part A, 132, pp. 231-238, 2002.

Kwon, H., Peiper, S., Kang, K., "Fiber Optic Immunosensors for Cardio-vascular Disease Diagnosis: Quantification of Protein C, Factor V Leiden, and Cardiac Troponin T in Plasma", Oxygen Transport to Tissue XXIII—Oxygen Measurements in the $21^{st}$ Century: Basic Techniques and Clinical Relevance, Adv. Exp. Biol. Med. 510: 115-119, 2003.

Lakowicz, Joseph R., et al., "Release of the self-quenching of fluorescence near silver metallic surfaces", Analytical Biochemistry 320 (2003) 13-20.

Ogert, R., Brown, J., Singh, B., Shriver-Lake, L., Ligler, F., "Detection of *Clostridium botulinum* Toxin a Using a Fiber Optic-Based Biosensor", Anal. Biochem. 205, pp. 306-312, 1992.

Oswald, B., Gruber, M., Bohmer, M., Lehmann, F., Probst, M., Wolfbeis, O., "Novel Diode Laser-compatible Fluorophones and their Application to Single Molecule Detection, Protein Labeling and Fluorescence Resonance Energy Transfer Immunoassay", Photochemistry and Photobiology, 74(2), pp. 237-245 (2001).

Ren, Y., Rezania, S., Kang, K., "Biosensor for Diagnosing Factor V Leiden, a Single Amino Acid Mutated Abnormality of Factor V", 2006, Adv. Exp. Med. Biol. 614: 245, 2008, Abs. only.

Rezania, S., Kang, K., "Separation of Factor V Leiden Molecule, a Mutated Form of Factor V, from Plasma of Homozygous Patient," Proceeding of the 2006 Annual Conference on the International Society of Oxygen Transport to Tissue, Louisville, KY (Aug. 12-17, 2006). , Adv. Exp. Med. Biol. 614: 101, 2008, Abstract only.

Rowe, C., Bolitho, J., Jane, A., Bundesen, P., Rylatt, D., Eisenberg, P., Liger, F., "Rapid Detection of D-dimer Using a Fiber Optic Biosensor", Thromb. Haemost. 79, pp. 94-98 (1998).

Spiker, J., Kang, K., Drohan, W., Bruley, D., "Preliminary Study of Biosensor Optimization for the Detection of Protein C", Advances in Experimental Medicine and Biology, 454, pp. 681-688 (1998).

Spiker, J., Kang, K., "Preliminary Study of Real-time Fiber Optic Based Protein C Biosensor", Biotechnology and Bioengineering, 66(3), pp. 158-163 (1999).

Spiker, J., Drohan, W., Kang, K., "Reusability Study of Fiber Optic Based Protein C Biosensor", Advances in Experimental Medicine and Biology, 471, pp. 731-739 (1999).

Trabesinger, W., Kramer, A., Kreiter, M., Hecht, B., Wild, U., "Single-molecule near-field Optical Energy Transfer Microscopy", Appl. Phys. Lett. 81(11), pp. 2118-2120, 2002.

Zhang, J., Chang, C., Miller, A., and Kang, K., "A Feasibility Study of Multispectral Image Analysis of Skin Tumors", Biomedical Instrumentation and Technology, 34(4), pp. 274-282, 2000.

* cited by examiner

FV 20-mers: H-I-C-K-S-R-S-L-D-R-R-G-I-Q-R-A-A-D-I-E-Q-NH$_2$ FVL 20-mers: H-I-C-K-S-R-S-L-D-R-Q-G-I-Q-R-A-A-D-I-E-Q-NH$_2$

SEQUENCE LISTING

```
<160> NUMBER OF SEQ ID NOS: 2

<210> SEQ ID NO 1
<211> LENGTH: 22
<212> TYPE: PRT
<213> ORGANISM: Artificial Sequence
<220> FEATURE:
<223> OTHER INFORMATION: Factor V

<400> SEQUENCE: 1

His Ile Cys Lys Ser Arg Ser Leu Asp Arg Arg Gly Ile Gln Arg Ala
1               5                   10                  15

Asp Ile Glu Gln Asn His
            20

<210> SEQ ID NO 2
<211> LENGTH: 22
<212> TYPE: PRT
<213> ORGANISM: Artificial Sequence
<220> FEATURE:
<221> NAME/KEY: MUTAGEN
<222> LOCATION: (11)..(11)
<223> OTHER INFORMATION: Factor V Leiden

<400> SEQUENCE: 2

His Ile Cys Lys Ser Arg Ser Leu Asp Arg Gln Gly Ile Gln Arg Ala
1               5                   10                  15

Asp Ile Glu Gln Asn His
            20
```

SENSORS AND METHODS FOR DETECTING DISEASES CAUSED BY A SINGLE POINT MUTATION

SEQUENCE LISTING

The present application includes a sequence listing in electronic format. The sequence listing is provided as a file entitled H10062.txt, which is hereby incorporated by reference in its entirety.

BACKGROUND OF THE INVENTION

Detection and diagnosis of disease is usually a necessary prerequisite to treatment and/or curing of the disease. With many inherited diseases, definitive diagnosis must often occur at a molecular level, and typically includes DNA analysis, which can be impractical and expensive owing to the complex and time-consuming procedure inherent to DNA testing. This is especially true of diseases caused by single point mutations, where the historical difficulty in obtaining purified monoclonal antibodies leaves DNA testing as the only viable method of diagnosing disease. While this is true for most diseases caused by single point mutations, one exemplary disease is a clotting disorder associated with a single point mutation of the gene encoding Factor V, known as Factor V Leiden.

To maintain a normal physiological system, it is crucial for blood to travel in an unobstructed manner through the vascular system. When injury occurs to the body, hemostasis assists in clot formation to prevent the loss of blood, while conversely, an anti-coagulant system ensures that the clot is localized at the site of damage, i.e., on the vessel wall, rather than inside blood vessels. Naturally, disturbances in the hemostatic system result in diminished ability to dissolve clots in blood vessels, which can cause traumatic thromboembolitic results. Thromboembolism may cause a variety of dangerous conditions within the body, such as deep vein thrombosis, lung embolism, stroke, and heart attack as normal blood flow from the heart to the body organs is blocked.

The most well-recognized inherited thrombophilic conditions include a resistance to the anti-coagulant Activated Protein C, as well as deficiencies of anti-coagulants, such as Protein C, Protein S, and Antithrombin III deficiencies. For example, Factor V is a blood coagulant that is inhibited by Activated Protein C, which, in turn, prevents blood coagulation. The single point mutation to Factor V, i.e., Factor V Leiden (FVL), causes a resistance to Activated Protein C, thereby preventing the inhibition of blood clotting.

FVL is the most common hereditary blood coagulation disorder in the United States. It is present in 5-8% of the Caucasian population and 1.2% of the African American population. FVL increases the risk of venous thrombosis approximately 3-8 fold for heterozygous and 30-140 folds for homozygous individuals.

Annually, as many as 600,000 hospitalizations and approximately 50,000 deaths are caused by pulmonary embolism alone. It has been estimated that death from pulmonary embolism results within 30 minutes on onset. Despite the widespread belief that FVL is responsible for a significant number of these hospitalizations and fatalities, clinicians do not routinely screen for FVL. This failure to screen may result, in part, from the lack of widely accepted detection methods.

Presently, most accurate FVL detection methods require DNA analysis, which are impractical for routine screening, as they are very expensive and time-consuming, and they do not provide a level for FVL in plasma. Consequently, FVL is usually screened with a clotting assay that is not sufficiently specific for FVL. Further, it can be difficult for a clotting assay to distinguish between FVL and other types of blood clotting disorders, such as deficiencies in Protein C or Antithrombin III. In fact, because FVL results in a resistance to Activated Protein C, FVL and Protein C deficiency may be indistinguishable with current assay protocols.

In view of the large population of affected individuals, early screening of FVL could make affected individuals aware of their high risk for thromboembolic complications and encourage them to take preventive actions. This may help to avoid the enormous after-care expenses incurred by victims—including physical debilitation and also emotional stress.

BRIEF SUMMARY OF THE INVENTION

Embodiments of the invention provide rapid and accurate diagnostic methods and immunological sensors for diagnosing diseases caused by a single point mutation. Exemplary embodiments of the invention provide rapid and accurate diagnostic methods and sensors for diagnosing single point mutations for biomolecules needed for normal physiological functions. A more particular example is blood clotting disorders associated with a genetic mutation known as Factor V Leiden (FVL). Other exemplary embodiments include methods for generating site-specific antibodies particular to a mutation site.

DETAILED DESCRIPTION OF THE PREFERRED EMBODIMENTS

Embodiments of the invention provide rapid and accurate diagnostic methods and immunological sensors for diagnosing diseases caused by a single or a few point mutation. Exemplary embodiments of the invention provide rapid and accurate diagnostic methods and sensors for diagnosing blood clotting disorders associated with a genetic mutation to the gene encoding normal Factor V (FVN), where the mutation is known as Factor V Leiden (FVL).

While it is contemplated that embodiments of the invention may be used to diagnose a variety of diseases, and is especially advantageous in diagnosing those diseases caused by a point mutation, the clotting disorder associated with FVL will be discussed herein for exemplary purposes.

Figure 1:
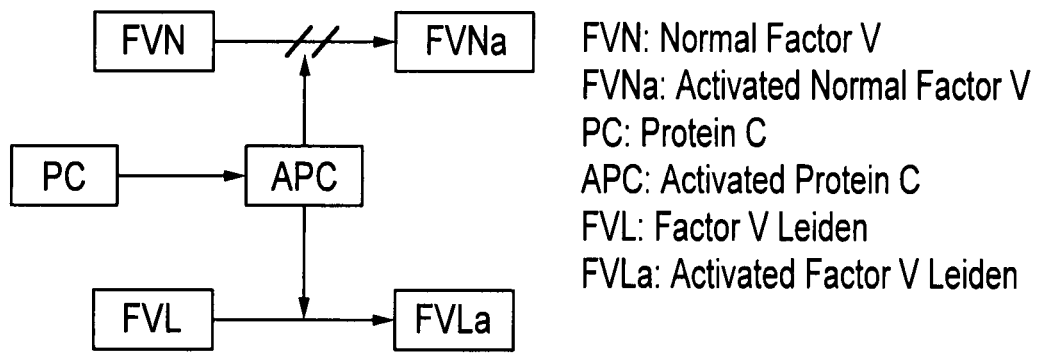
FIG. 1 is a schematic diagram illustrating the role of Normal Factor V (FVN), activated Normal Factor V (FVNa), Factor V Leiden (FVL), activated Factor V Leiden (FVLa), Protein C (PC), and activated Protein C (APC)

FVN is a single-chain glycoprotein (MW=330,000) that circulates in blood at 4-14 µg/ml. Activated Normal Factor V (FVNa) is one of the necessary components in the process of clot formation. Activated Protein C (APC) is an anticoagulant and serine protease that down-regulates thrombin formation by inactivating the activated blood coagulants, FVNa and Factor VIII (FVIIIa). FIG. 1 illustrates the blood coagulation/anticoagulation pathway, including the roles of APC, FVN, and FVNa.

FVL is a mutation to the heavy chain of the Factor V molecule, and is the most common (>90%) mutation to FVN, where FVL possesses an amino acid substitution ($Arg_{506} \rightarrow Gln_{506}$). This amino acid substitution results in activated FVL (FVLa), which is consequently not inactivated by the APC (as also shown in FIG. 1), thereby resulting in a condition that is accordingly referenced as "APC resistance." The FVN and FVL molecules are equally well activated by thrombin and have the same cofactor activity in prothrombin activation. Functional differences between FVN and FVL only become apparent during the inactivation cascade, i.e., FVL does not get inactivated by APC and therefore the individuals with FVL have hypercoagulation (blood clotting) problems.

The heterozygous form of FVL has been estimated to occur in 3% to 7% of Caucasians, while the homozygous state has been estimated to occur in 1 in 5000 individuals. Also, this defect has been found in approximately 30% of patients with previously unexplained thrombotic disease and associated with a number of obstetrical pathological situations such as fetal loss, preeclampsia and HELLP syndrome.

Figure 2:
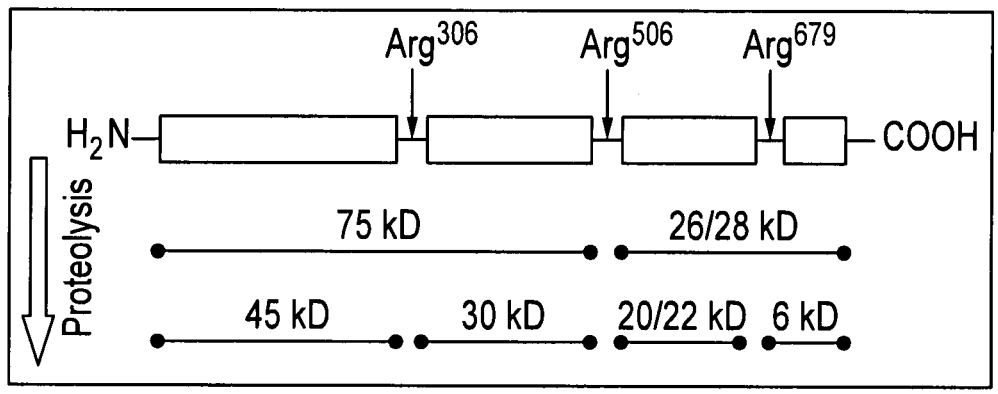
FIG. 2 is a schematic diagram illustrating the sites of proteolysis of the heavy chain of FVN molecule.

As illustrated in FIG. 2, during a normal inactivation cascade of activated FVN (FVNa), as in healthy individuals, inactivation is achieved via proteolysis of the heavy chain of FVNa by APC at three positions of FVNa, in the following order: $Arg_{506}$, $Arg_{306}$, and $Arg_{679}$. Inactivation of FVNa appears to be a biphasic reaction that consists of a rapid phase, during which nearly 50% of the FVNa activity is lost. This is followed by a second, slow phase that completes inactivation. Cleavage at $Arg_{506}$ generates a 75 kD fragment and a 28/26 kD doublet. This proteolysis is necessary for the optimum exposure of the sites for subsequent cleavage at $Arg_{306}$ and $Arg_{679}$.

Proteolysis at these sites leads to the appearance of 45 kD, 30 kD, and 6 kD fragments, as well as a 22/20 kD doublet. Cleavage at $Arg_{306}$ is membrane-dependent and is required for complete inactivation.

Figure 3:
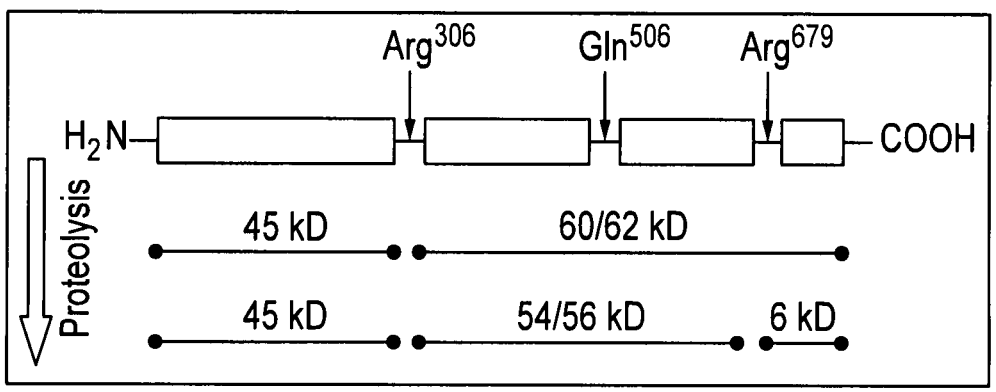
FIG. 3 is a schematic diagram illustrating the abnormal sites (mutated from Arg to Gln) of the heavy chain of FVL molecule and its proteolysis.

In contrast, and as illustrated in FIG. 3, proteolysis of the FVLa molecule by APC occurs in the order of $Arg_{306}$ and $Arg_{679}$. Cleavage at $Arg_{306}$ produces a 45 kD fragment and a 62/60 kD doublet. Subsequently, the 62/60 kD doublet is cleaved at $Arg_{679}$ to generate a 6 kD fragment and a 56/54 kD doublet, as illustrated in FIG. 2. Notably, the FVL molecule has mutation at $Arg_{506}$ that leads to $Gln_{506}$. This site is not available to APC proteolysis. This results in complete loss of cofactor activity.

Since the $Arg_{306}$ and $Arg_{679}$ sites of FVL are not optimally available to APC (due to no cleavage at the mutated $Gln_{506}$ site), inactivation of FVLa (i.e., blocking of its coagulation function) is much slower than that of FVNa. Inactivation of FVLa occurs at a rate that is approximately similar to that of the second phase of normal FVNa inactivation. For example, while FVNa loses nearly all of its cofactor activity following 5 min of incubation with APC, the FVLa molecule only loses 50% of its activity during the same period. Moreover, following 60 minutes, FVLa still retained between 10-20% of its activity. This impaired down-regulation of FVLa allows the molecule to linger at the place of vascular injury, thereby promoting the increased risk of thrombosis.

Conventional methods of FVL diagnosis involve DNA analysis, resulting in an unduly long assay time with an associated high cost. Additionally, because FVL is the result of a point mutation, it is difficult to obtain an antibody with a high degree of specificity to FVL without cross reacting with FVN.

Embodiments of the invention provide immunological methods and sensors for detecting the presence and quantities of FVN and FVL, respectively, to accurately diagnose individuals having the FVL allele(s) as being either heterozygous or homozygous for the FVL allele. By quantifying the respective FVN and FVL molecules, the extent of normality or abnormality of the individual may be determined.

The methods and sensors of the invention are especially advantageous because embodiments of the invention provide antibodies specific to FVL molecules, promoting more precise and accurate detection and quantification of FVL for diagnosis of a disease condition. Embodiments of the invention may be used in real-time to diagnose FVL and FVN deficiency insofar as a patient's plasma may be used as the sample under analysis. Additionally, embodiments of the invention provide a short assay time, on the order of approximately 3-15 minutes. Enhanced sensitivity provided by exemplary methods allows use of small-sized (as nonlimiting examples, 1.5 cm×2.0 cm) chips to be used for a microchip sensor system. Further, due to the small sensor sizes available, a small sample volume can be used (as nonlimiting examples, 0.3 ml-0.5 ml). Cost associated with diagnosis is minimized, as compared to conventional methods (e.g., DNA analysis) of diagnosis. Embodiments promote ease of use, promoting use as a general screening sensor and method. By providing knowledge of the abnormality early to the FVL patients, the patients are able to prepare for the immediate treatment methods when thromboembolic episodes occur. In return, it will reduce the healthcare cost tremendously because, if thromboembolic episodes are not immediately treated, the cost of possible traumatic consequences is enormous.

A first preferred embodiment of the invention provides for a method of generating antibodies specific to the site with the abnormality (a single amino acid mutation site) of the molecule. In this manner, antibodies may be created with a high specificity and high accuracy to particular mutation sites of particular target molecules, such as FVN and FVL, thus enabling one to distinguish between the normal protein and the mutated variant with greater specificity. While it is contemplated that the method may be used to generate antibodies specific to a variety of genetic sequences that include single point mutations, for exemplary purposes, antibodies specific to FVN and FVL will be discussed in conjunction with the first preferred method.

According to the first preferred embodiment, non-mutant-preferable and mutant-preferable antibodies are obtained by creating antigenic synthetic precursor peptides having a predetermined length that correspond individually to normal and mutated molecules, respectively. Preferably, the respective antibodies approach total mutual exclusivity to one or the other of the normal or mutant molecules, such that there is little to no cross reactivity. In this way, each antibody ideally approaches mutually exclusive reactivity with only one of a normal or mutated molecule.

Figures 4, 5:
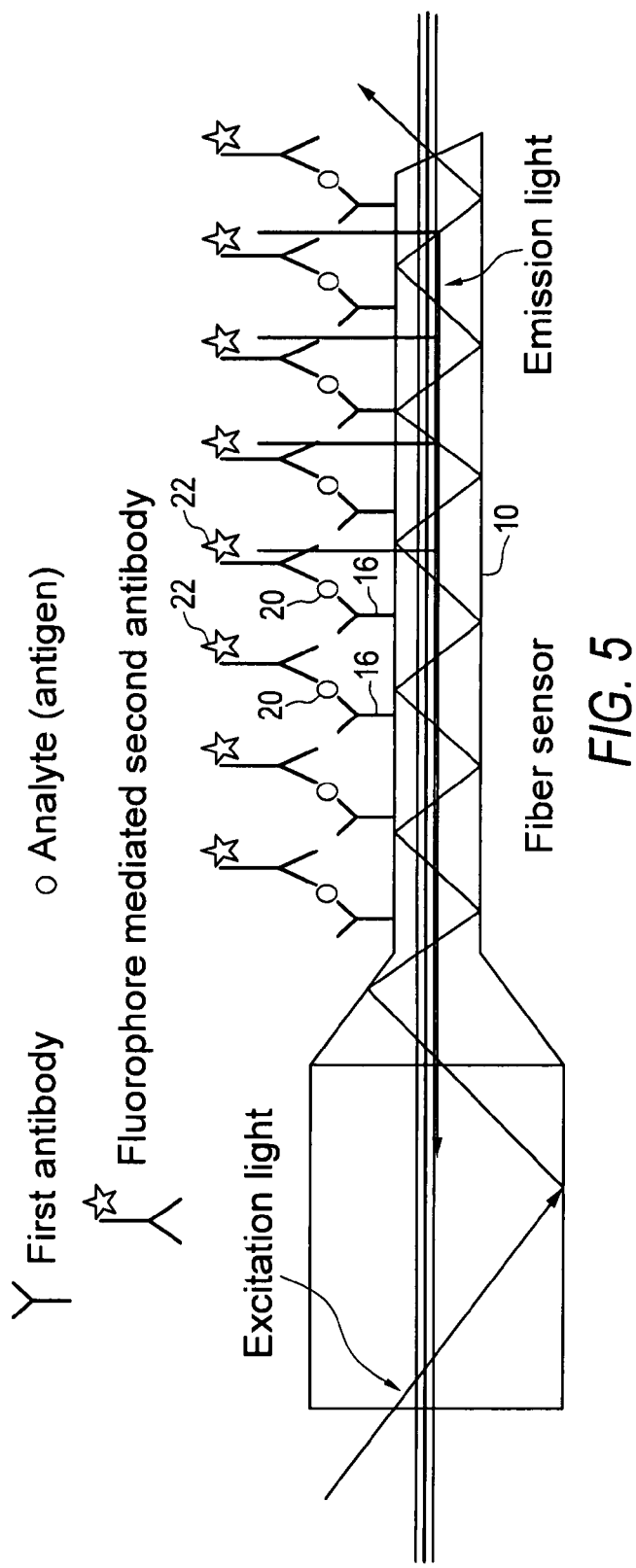
FIG. 4 is a schematic diagram illustrating two 20-mer peptides of FVN and FVL used to generate antibodies according to an embodiment of the invention.
FIG. 5 is a schematic diagram illustrating a sandwich immunoassay on an optical fiber according to an embodiment of the invention.

For exemplary purposes, the instant embodiment will be shown and described in connection with the FVN and FVL molecules. For example, FVN-preferable and FVL-preferable antibodies are obtained by creating antigenic synthetic precursor peptides having a predetermined length and corresponding individually to FVN and FVL, herein referenced as the "FVN peptide" (SEQ ID NO: 1) and the "FVL peptide" (SEQ ID NO: 2). While the number of amino acid residues in each of the FVN and FVL peptides may vary to suit individual applications, the peptides include the target cleavage site, either in its non-mutated form for the FVN peptide ($Arg_{506}$) or its mutated form for the FVL peptide ($Gln_{506}$). In the preferred embodiment, each of the FVN (SEQ ID NO: 1) and FVL peptides (SEQ ID NO: 2) are 20 amino acid residues ("20-mers") in length, as illustrated in FIG. 4. The FVN peptides (SEQ ID NO: 1) and FVL peptides (SEQ ID NO: 2) are then conjugated to carrier molecules via a terminal cysteine residue to serve as immunogens, with which multiple hybridoma cell lines may be derived, such as from immunized mice.

A hybridoma is a hybrid cell produced by injecting a specific foreign antigen into a host animal, such as a mouse, collecting an antibody-producing cell from the host's spleen, and fusing it with a long-lived cancerous immune cell called a myeloma cell. Individual hybridoma cells are cloned and tested to find those that produce the desired antibody. Their many identical daughter clones will secrete, over a long period of time, millions of identical copies of made-to-order "monoclonal" antibodies.

The antibodies resulting from the hybridoma technique yield the FVN-preferable and FVL-preferable antibodies, as confirmed by initially screening the antibodies with the 20-mers. After the initial screening, the selected antibodies are again screened using the FVN molecule (native FVN molecule) and the FVL molecule (native FVL molecule). As a result of this additional screening, antibodies with high affinity to FVL molecules that have limited to no cross-reactivity with FVN are selected to obtain the FVL-preferable antibodies. Similarly, antibodies with high affinity to FVN molecules that have limited to no cross-reactivity with FVL are selected to obtain the FVN-preferable antibodies. The FVN-preferable and FVL-preferable antibodies are therefore more specific against the mutation site rather than to the entire molecule, which gives a better probability to obtain antibodies specific to that site.

Another preferred embodiment of the invention includes a method of using non-mutant-preferable antibodies and mutant-preferable antibodies to detect and quantify non-mutant and mutant variants of a protein to diagnose individuals having a particular allele(s). For example, the instant preferred embodiment includes a method of using FVN-preferable antibodies and FVL-preferable antibodies to quantify FVN and FVL, respectively, to diagnose individuals having the FVL allele(s). Further, by quantifying FVN and FVL, methods of the invention may be used to determine the genotype of the individual (i.e., heterozygous or homozygous) and the extent of affliction, if any.

More particularly, by using known sensitivities of a combination of antibodies that include one or more of 1) commercial antibodies against the light chain (light chain antibodies) of FVL or FVN (these antibodies are reactive to epitopes of both FVL and FVN because FVL is a mutation to only the heavy chain of the molecule); 2) FVL-preferable antibodies; and 3) FVN-preferable antibodies, presence and quantity of FVL and FVN in a sample, as well as Total Factor V (FVT), may be determined. Total Factor V (FVT) is the amount of normal Factor V (FVN) plus the amount of Factor V Leiden (FVL). Once detected and quantified, the method provides for determine the genotype of the individual (i.e., heterozygous or homozygous) and degree of affliction.

The instant preferred method includes obtaining FVL-preferable antibodies and FVN-preferable antibodies and subsequently quantifying the amount of FVL and FVN in a sample, such as plasma. Using known or experimentally ascertainable affinities of each of the FVL-preferable and FVN-preferable antibodies for the respective FVL and FVN molecules, a system of equations may be employed and solved to determine values of the unknown variables that represent the respective quantities of FVL and FVN. The variables may be used to determine the degree to which a patient is afflicted with FVL, as well as make a determination as to the patient's homozygosity or heterozygosity.

Preferably, a commercial light chain antibody is also screened against the sample. Because a commercial light chain antibody has generally equal affinity for FVL and FVN, a commercial light chain antibody will be used as a second antibody for the sandwich assay. Once the amount of FVL and FVN in a sample is determined then the total amount of Factor V (FVT) will be determined. Since this sensing system provides the FVT in plasma it can also diagnose FVN deficiency.

Having obtained FVN-preferable and FVL-preferable antibodies, a sample may then be selectively exposed to each type of antibody with separate FVN and FVL optical sensors. Signal intensities are obtained from exposure of the sample to the antibodies on the respective optical sensors, which may then be used to solve for quantities of each of FVL and FVN present in the sample.

More particularly, as illustrated in FIG. 5, one preferred method includes exposing a sample serially or simultaneously to a pair of optical fibers, where each of the optical fibers bears either immobilized FVN-preferable or FVL-preferable antibodies. After exposure to the sample, the system is preferably probed with a fluorophore-tagged 2° monoclonal antibody (Mab) against FVT (antibody against the light chain), which binds both FVN and FVL ubiquitously.

While the invention contemplates use of a variety of fluorophores, one exemplary fluorophore is Alexa fluorophore 647™ (AF647), such that the tagged 2° Mab is AF647-2°Mab. Light of a suitable wavelength, such as approximately 635 nm for example, is applied through the optical fibers, and the specifically bound AF647-2° Mab will generate fluorescence at a level proportional to the concentration of FVN or FVL in the sample. Fluorescence may be measured with a fluorometer, whereby the fluorescence intensity is correlated to the amount of antigen in a sample.

For example, a sample with only FVL and without FVN will exhibit a signal intensity to the sensor with FVL preferable sensor according to the following equation:

$$FVL\ only:\ SI_{FVL} = A_{FVL} \times C_{FVL} \tag{EQ1}$$

where "SI" represents "signal intensity," "A" represents the slope of the standard curve showing the relationship between the FVL concentration and the signal intensity, and "$C_{FVL}$" represents concentration of the FVL. The slope A may be determined, for example, by obtaining standard curves using samples with only FVN or FVL in plasma.

Similarly, a sample with only FVN and without FVL will exhibit a signal intensity according to the following equation:

$$FVN\ only:\ SI_{FVN} = A_{FVN} \times C_{FVN} \tag{EQ2}$$

where "SI" represents "signal intensity," "A" represents slope of the standard curve showing the relationship between the FVN concentration and the signal intensity, and "$C_{FVN}$" represents concentration of the FVN.

Accordingly, the total signal intensity obtained from both reactions (pure FVL and pure FVN) may be expressed by the following equation:

$$SI_{TOTAL}\ for\ FVL\ preferable\ sensor = A_{FVL} \times C_{FVL} + A_{FVN} \times C_{FVN} \tag{EQ3}$$

Using the same concept, the total sensing signal from an FVN preferable sensor can be expressed as follows:

$$SI_{TOTAL}\ for\ FVN\ preferable\ sensor = B_{FVL} \times C_{FVL} + B_{FVN} \times C_{FVN} \tag{EQ4}$$

Where $B_{FVL}$ and $B_{FVN}$ are the slopes of the standard curve for the FVN preferable sensor.

Because there are two unknowns, where the two unknowns are the respective concentrations of FVL ($C_{FVL}$) and FVN ($C_{FVN}$), a system of equations (EQ3 and EQ4) is employed to solve for each of the two values.

In this way, values calculated for $C_{FVL}$ and $C_{FVN}$ may be compared to values associated with healthy or disease-causing levels of FVL, with enough specificity to determine whether an individual is normal (FVN), heterozygous (FVN/FVL) or homozygous (FVL/FVL) for the disease. For example, a normal range of FVN in a healthy (not having the allele) individual is between 4 and 14 micrograms/mL with no FVL.

In another embodiment, three equations may be employed as a check of the results associated with FVN and FVL concentrations. More particularly, in addition to the FVN-preferable and FVL-preferable antibodies against respective sequences of the heavy chain, antibodies against the light chain of FVN, such as those commercially available and known in the art, may also be used. The light chain antibodies have slightly different yet ascertainable affinities for each of FVL and FVN. As such, exposure of the sample to the third, and relatively ubiquitous antibody, acts as a further check in the system of equations.

One exemplary system of equations that includes signal intensity data from a third optical sensor is as follows:

$$SI_{TOTAL}\ for\ FVL\ preferable\ sensor = A_{FVL} \times C_{FVL} + A_{FVN} \times C_{FVN} \tag{EQ5}$$

$$SI_{TOTAL}\ for\ FVN\ preferable\ sensor = B_{FVL} \times C_{FVL} + B_{FVN} \times C_{FVN} \tag{EQ6}$$

$$SI_{TOTAL}\ for\ the\ third\ sensor = D_{FVL} \times C_{FVL} + D_{FVN} \times C_{FVN} \tag{EQ7}$$

where $D_{FVL}$ and $D_{FVN}$ are the slopes of the standard curve for the FVL and FVN respectively, for the third sensor developed using the commercially available two different monoclonal antibodies generated against the light chain of the molecule.

While embodiments of the method have been described as using two and three optical sensors, respectively, it is contemplated by the invention that an artisan may employ additional optical sensors to enhance the precision and accuracy of the sample analysis by employing a system of equations where the number of equations is commensurate with the number of optical sensors employed in the method.

Other embodiments of the invention provide immunological sensors that include mutant-preferable and non-mutant-preferable antibodies for detecting the presence and quantities of FVN and FVL, respectively, to accurately diagnose individuals heterozygous and homozygous for the FVL allele.

Figure 7:
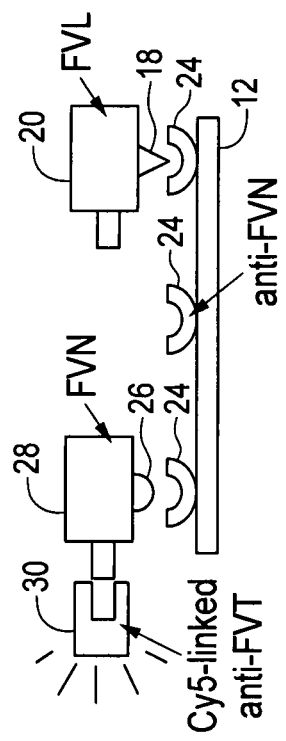
FIG. 7 is a schematic diagram of a sandwich immunoassay on an FVN-preferred sensing fiber according to an embodiment of the invention.
Figure 8:
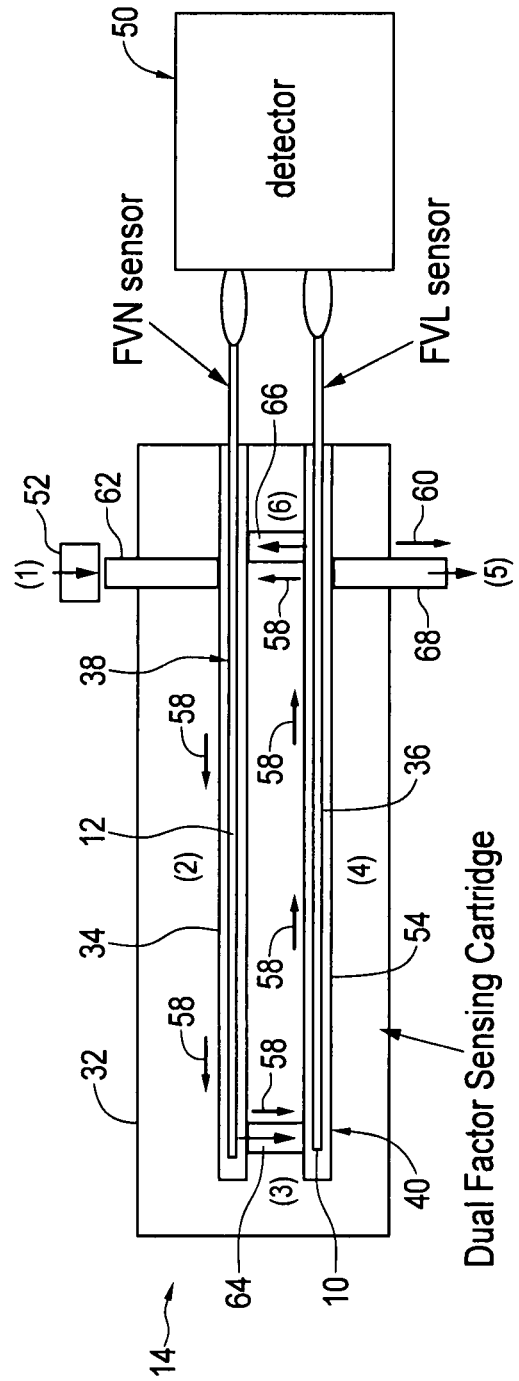
FIG. 8 is a schematic diagram of two optical fiber immunosensors, one for FVN and one for FVL, according to a preferred embodiment of the invention.

As illustrated in FIG. 5, preferred embodiments of the immunological sensor include two or more optical fibers configured to have a sandwich fluoro-immunoassay performed thereon. More particularly, an optical FVL-sensing fiber 10 is illustrated generally in FIG. 6, an optical FVN-sensing fiber 12 is illustrated generally in FIG. 7, and a sensor, generally at 14, that includes both the FVL-sensing fiber and FVN-sensing fiber is illustrated in FIG. 8.

Figure 9:
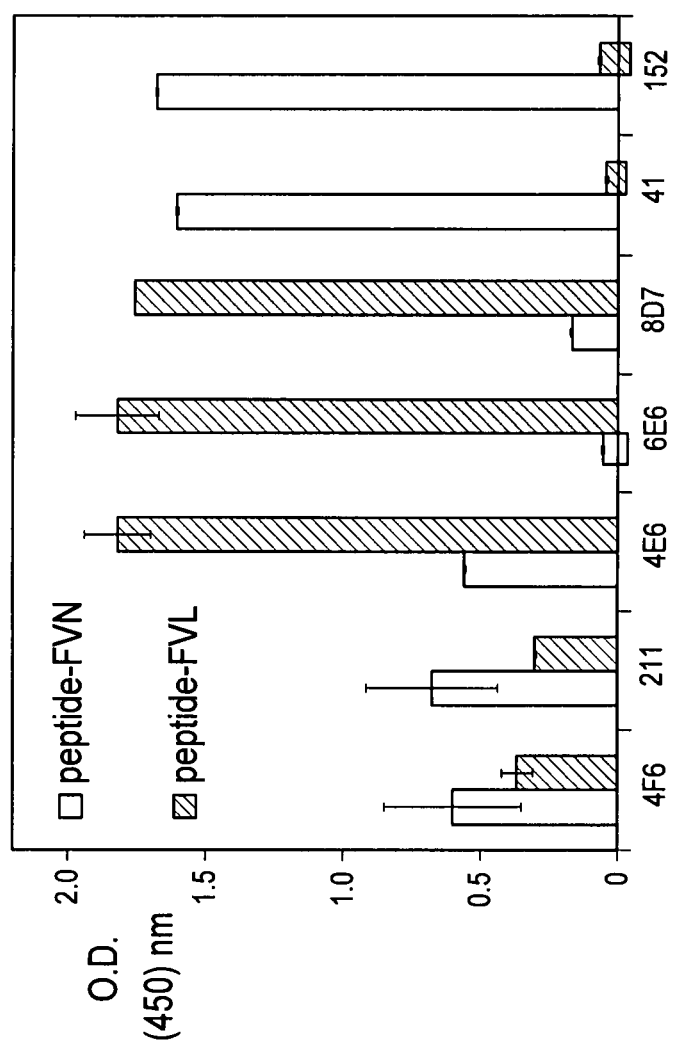
FIG. 9 is a graph illustrating an affinity of antibodies to peptides using enzyme linked immunoabsorbent assay (ELISA)

A surface of the FVL-sensing fiber 10 preferably includes an FVL 1°Mab 16 against the FVL mutant cleavage site 18 ("anti-FVL"), which is designated as 6E6 or 8D7 in FIG. 9. When FVL 20 binds to the FVL 1° Mab 16, a Cy5-linked anti-FVT 2° Mab 22 binds FVL and will fluoresce to indicate the presence of FVL. Similarly, a surface of the FVN-sensing fiber 12 includes an FVN 1° Mab 24 against the FVN site 26 (anti-FVN) corresponding to the mutant cleavage site of FVN 28. A Cy5-linked anti-FVT 2° Mab 30 will bind FVN and fluoresce to indicate the presence of FVN. The order in which the 1° Mab and 2° Mab are used in the sensor may be reversed.

While the optical sensing fibers 10, 12 may be remote from one another, the preferred immunological sensor 14 (FIG. 8) is configured such that the two optical sensing fibers are in fluid communication with one another such that a sample may be passed simultaneously or serially over each optical sensing fiber.

More particularly, the two optical-sensing fibers 10, 12 are preferably placed in a platform, such as a cartridge 32, to form a dual sensing system. Since the two fiber system is preferably interconnected, the optical sensing fibers 10, 12 are preferably in close proximity, which optimizes the overall size of the system. One preferred platform is the cartridge 32 having two grooves 34, 36 disposed therein, wherein a first of the grooves 34 is configured to receive an FVN sensing unit 38 that houses the FVN-sensing fiber 12 and the other of the grooves 36 is configured to receive an FVL sensing unit 40 that houses the FVL-sensing fiber 10.

Example FVN and FVL sensing units 38, 40 may advantageously be prepared separately and subsequently coupled to the cartridge 32, which controls the timing and flow velocity, by the use of micro-electro-mechanical system (MEMS) technique. Within a particular example sensing unit 38, 40, an FVN optical-sensing fiber 12 is placed within a sample chamber such as, but not limited to, a glass tube where a sample, such as plasma, is injected. Suitable fluid inlet and outlet ports (such as, but not limited to, a valve such as a T-valve) lead into and out of the sample chamber, respectively. The sensing units 38, 40 include an immuno-optical sensor within a predetermined length of the sensing chamber, for example a 3 cm length of the glass tube. While a volume of the sensing units 38, 40 may vary, one exemplary volume is approximately 100 μl.

In FIG. 8, sensing units 38 and 40 are connected, and valves 52, 66, and 68 are provided to maintain the sample in a circulation/incubation circuit, indicated by the arrows at 58, or to alternatively discharge the sample, indicated by arrows at 60. The cartridge 32 is preferably manufactured using any one of suitable materials, such as soda lime glass, silicon or polymeric substrates as Plexiglas in the future, which promotes easy sterilization. Preferably, the cartridge 32 is a microchip.

As illustrated in FIG. 8, an inlet 62 is configured to receive a sample via injection or other means. A micro pumping system (for example, valve 52) circulates the sample through the FVN sensing unit 38 and the FVL sensing unit 40, which are fluidly coupled via channels 64, 66, for a predetermined period of time. After the sample is incubated, an outlet 68 is provided for sample discharge. The detector 50 is also preferably provided to detect and record signal intensities emitted by the optical sensing fibers.

Still other embodiments of the invention include a dual sensor embodied in a MEMS device. A MEMS device includes a minimized sized probe; automatically controlled convective sample/reagent application; minimized sensing time; sensor reusability, waste disposal to avoid the possible blood born pathogens, etc. The assay protocol will be automated to make the sensor user-friendly and to eliminate the human error. These features may be realized with MEMS scaled microchannels to deliver sample to the sensor and to permit evacuation of sample from the sensor after an analysis has been conducted.

Figure 6:
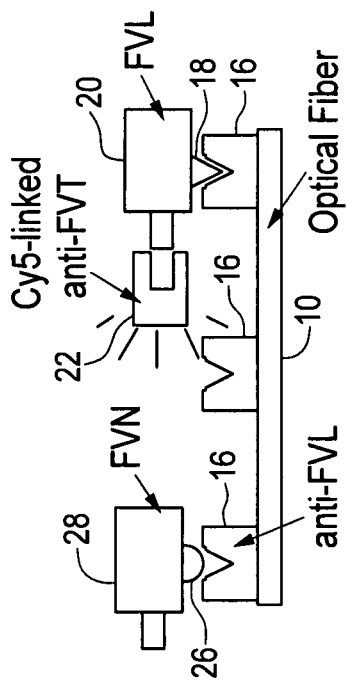
FIG. 6 is a schematic diagram of a sandwich immunoassay on an FVL-preferred sensing fiber according to an embodiment of the invention.

Sensing methods associated with the immunological biosensor are also provided by the invention. Each of the FVL-sensing and FVN-sensing fibers 10, 12 in FIGS. 6 and 7 are exposed to a sample, such as a plasma sample, and incubated for a period of time sufficient for target molecules (FVL 20 and FVN 28) to bind the respective antibodies 16, 24. While incubation times may vary to suit individual applications, one preferred incubation time is approximately 3 minutes.

Following incubation, as illustrated in FIG. 6, the FVL-sensing 10 fiber is preferably washed with washing buffer. Next, the system is probed with AF647 (fluorophore) tagged 2° Mabs 22 against an epitope that is shared by both FVN and FVL ("anti-FVT" against light chain). Commercially available monoclonal antibodies developed for the light chain of FV are sufficient for use as a reagent. Excitation light will be applied through the FVL-sensing fiber 10, and AF647-2° Mabs will generate fluorescence at a level proportional to FVL 20 only.

In the FVN-sensing fiber 12, illustrated in FIG. 7, the FVN 1° Mabs 24 attached to the fiber surface will be directed to the region of FVN 28 corresponding to the FVN mutant cleavage site 26 (anti-FVN). This will allow FVN 28 to preferably bind to the fiber, while minimizing (preferably approaching excluding) the binding of FVL 20. AF647-2° Mab (anti-FVT) used in this fiber system will be the same as that used in the first system. Once excitation light is applied through the FVN-sensing fiber 12, the specifically attached AF647-2° Mabs 30 will generate fluorescence at a level proportional to the concentration of only (or nearly only) FVN 28.

It is contemplated by the invention that the two fibers 10, 12 may be integrated in a dual sensing system, providing a simultaneous quantification of FVL and FVN, thereby providing a rapid and complete quantitative information on this particular abnormality.

The ratio of FVL to FVN can provide the level of thrombophilia, because the average total FV concentration in plasma deviates significantly (4-14 µg/ml). This is also useful for the development of an appropriate treatment plan for the patient.

Results and Discussion

While various methods may be used to prepare the optical sensing fibers, sensing sample, and antibodies, exemplary methods are provided herein. To increase the probability for generating antibodies against the mutated site, 20 amino acid sequences of FVN or FVL around the mutation region were generated (FIG. 4). The 20-mers conjugated with carrier protein were injected to mice and cell lines were generated using the hybridoma technique. The resulting antibodies were initially screened with the 20-mers. Antibodies with high affinity to FVL molecules without cross-reacting with FVN, and vice verse, were selected.

For testing the affinity of the antibodies generated, ELISA was performed as follows: 96 well microtiter plates were coated with 2 µg/ml of FVN in FVN free plasma and FVL homozygous plasma. After blocking with 1% Bovine Serum Albumin (BSA), the antibodies (1 µg/ml) was applied and a ½ serial dilution were performed. Then 1:1000 rabbit anti-mouse IgG Fc (gamma) specific, HRP conjugated was applied. After adding OPD solution, optical density was measured at 450 nm in ELISA reader.

Figure 10:
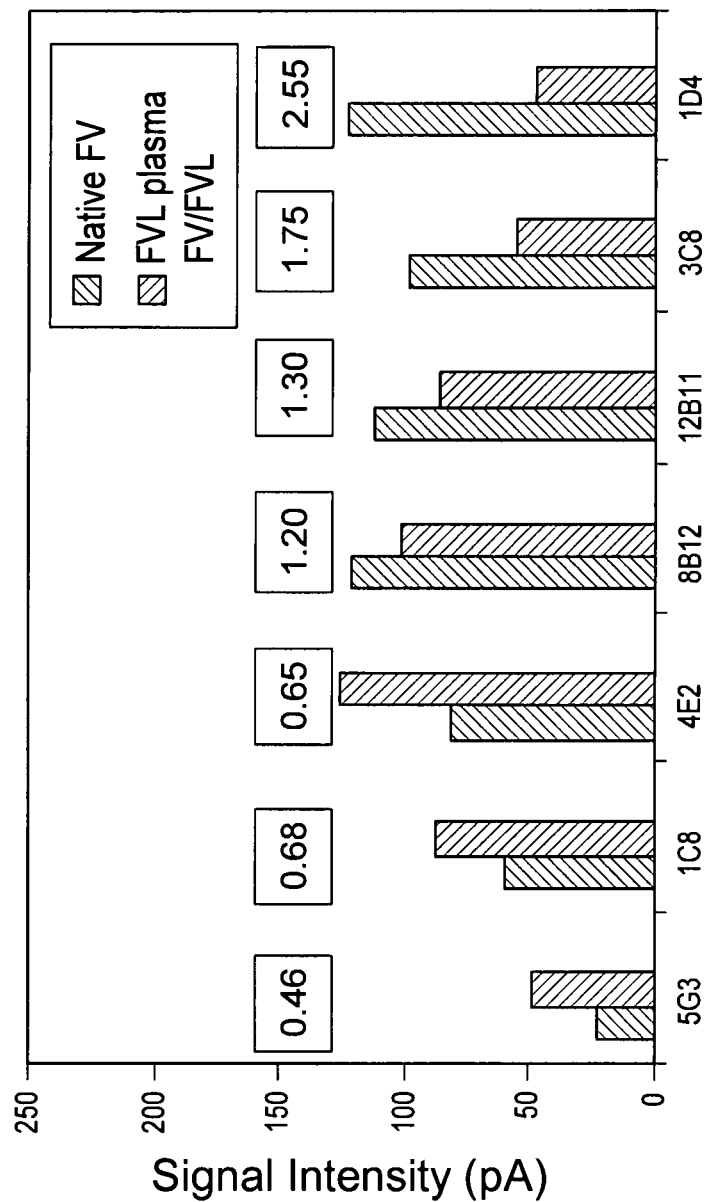
FIG. 10 illustrates the sensitivity of sensors developed with the derived antibodies, for native FVN and FVL molecules in plasma.

FIG. 10 illustrates the ratios of the signal intensity of native FVN molecules to FVL in sensing results increased from 5G3 to 1D4 antibodies. The ratio represented the affinity ratio of an antibody to FVN over that antibody to FVL. Antibody 5G3 is FVL preferred and 1D4 is FVN preferred. Therefore, 5G3 and 1D4 was selected to be 1°Mab in FVL preferred sensor and FVN preferred sensor, respectively.

Since both FVN and FVL molecules have the same amino acid sequence in light chain, each antibody against light chain is supposed to have the same binding site and the affinity to both FVN and FVL molecules. The 2°Mab for FVN preferable antibody and FVL-preferable antibody are preferably the same in a single sensing system. Therefore, a commercial light chain antibody, such as from Haematologic Tech., was determined as the 2°Mab for these sensors.

The core of the FVL and FVN sensors used in the exemplary method are tapered quartz fibers. The antibody against FVN or FVL (1° Mab) is immobilized on the fiber surface and then the fiber is enclosed in a sample chamber. When the sample is injected into the chamber, the FVN/FVL molecules are captured by the 1° Mab. After washing the fiber surface to remove unbound bio-molecules, another type of antibody (2° Mab) linked with fluorophores is applied to the sensing chamber. After the sandwich complex is formed, the emitted fluorescence is measured by a fluorometer. The fluorescence intensity is correlated with the amount of antigens in the sample.

When these generated monoclonal antibodies were tested with native FVN molecules or FVL plasma, they were found to be not specific to only one antigen but some had higher affinity to FVN and some with FVL and vice verse. The affinities of these antibodies were also expressed with the signal intensities of native FVN molecules and FVL plasma by using the fiber optical sensing system, where the generated antibodies were used as the 1°Mab in the sensor. The sensing experiments were performed with 10 cm sensor, 10/10 min incubation time and 1.2 cm/s circulation flow velocity.

Figure 11A:
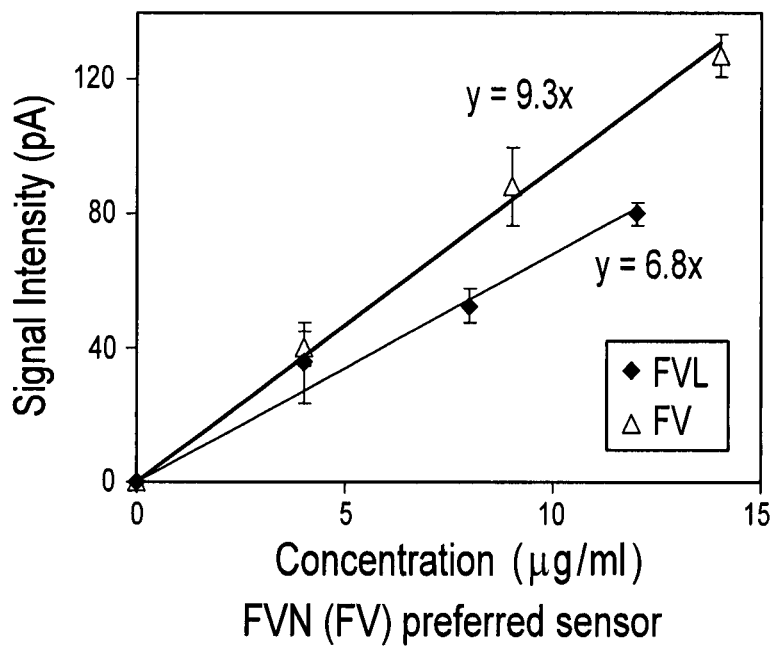
FIGS. 11A and 11B are graphs illustrating exemplary standard curves for exemplary FVN and FVL preferred sensors for FV or FV molecules.
Figure 11B:
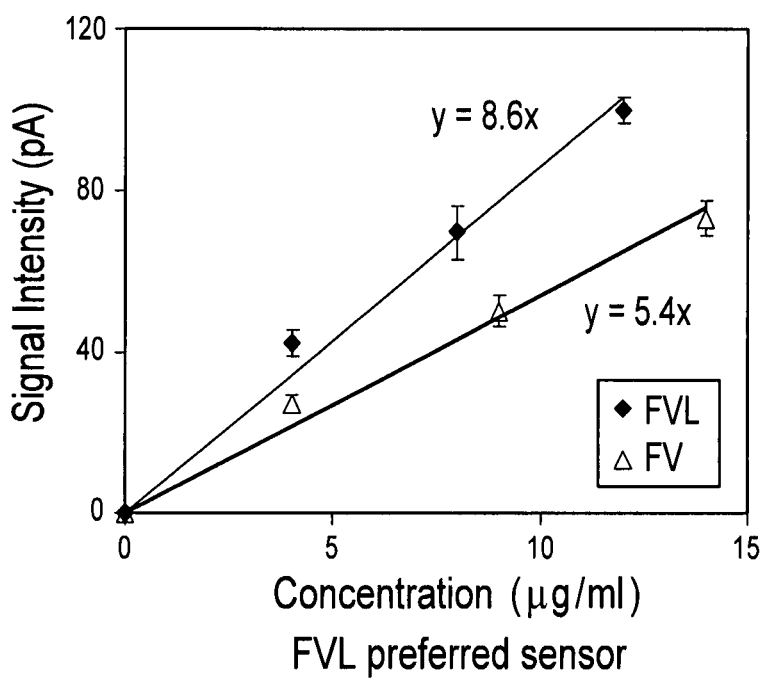

These two sensors—FVL preferred and FVN preferred—could be used for quantifying FVN and FVL molecules in the sample. The abilities of these sensors to sense the FVN or FVL separately are illustrated in FIGS. 11A and 11B. The sensing experiments were performed with 3 cm sensor, 3/2 min incubation time and 1.2 cm/s circulation flow velocity.

The standard curves were achieved under the pre-described sensing conditions within the interested sensing range (0-14 µg/ml for FVN; 0-12 µg/ml for FVL). The apparent reaction in fiber optical sensing system is slight diffusion limited for Protein C sensing. Since the molecules weight of FVN is 5 times larger than Protein C and the kinetic characters in all immuno-reactions, binding reaction between antibody and antigen, are similar, the apparent reactions in FVN preferred and FVL preferred sensor should also be diffusion limited. Under the certain sensing condition, the signal intensity is approximately linear with the concentration of analytes. FIGS. 11A and 11B illustrate the relationship between signal intensity and the concentration of FV molecules was linear in FVN and FVL preferred sensors. For FVL molecules, the relationship between signal intensity and concentration was also linear under the same experimental conditions.

Figure 12A:
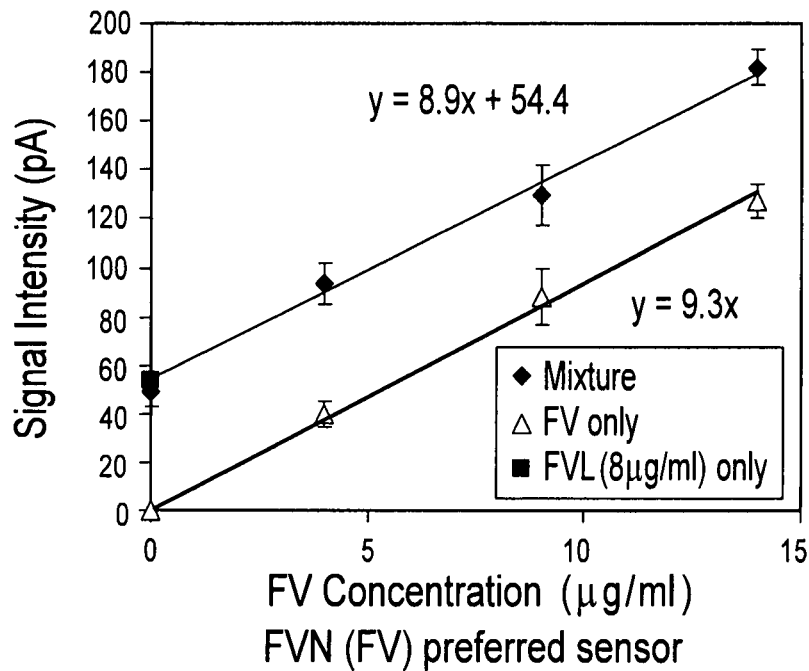
FIG. 12A is a graph illustrating exemplary sensing performance of the FVN preferred sensor for the samples of various amounts of FVN only, FVL at 8 microgram/ml, and the mixture of various amounts of FVN and FVL at 8 microgram/ml.
Figure 12B:
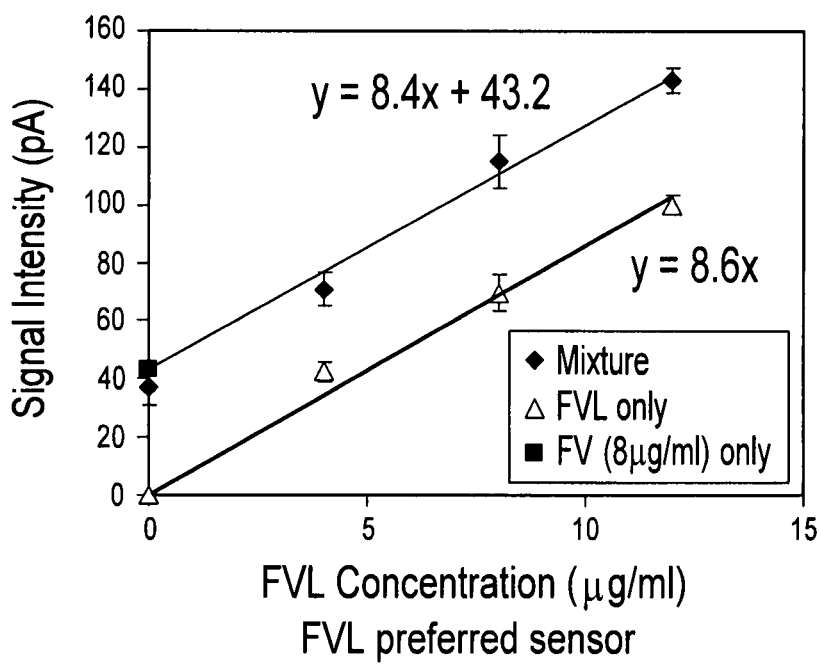
FIG. 12B is a graph illustrating exemplary sensing performance of the FVL preferred sensors for the samples of various amounts of FVL only, of FVN at 8 microgram/ml, and the mixture of various amounts of FVL and FVN at 8 microgram/ml.

The FVN and FVL mixture samples with a fixed FVL concentration (8 µg/ml) were measured by using FVN-preferred sensor. FIG. 12A illustrates the signal intensity of the mixture was linear with the concentration of FV in sample with the slope 8.9, which is similar with the slope of the standard curve of FVN for FVN-preferred sensor, and the preset intercept 54.4, which is exactly same with the signal intensity of the only FVN plasma sample (8 µg/ml) for this sensor. The signal intensity of the mixture is only the physical addition of the signal intensity of FVN and FVL. Therefore, FVL molecules do not affect the affinity to FVN in FVN-preferred sensor. FIG. 12B also illustrates that FVN molecules do not affect the affinity to FVL in FVL-preferred sensor.

In summary, the similarity of the amino acid sequence of FVN and FVL molecule posed challenges to the quantification of both molecules. The fiber optical sensors and methods provide rapid and accurate quantifications of the protein (FVL and/or FVN) in blood plasma, but it requires specific antibodies. In order to increase probability for specific antibodies, 20-mers were used to generate antibodies against FVN or FVL only. Resulting antibodies with high respective affinities to FVN or FVL were chosen as 1°MAb of the FVN or FVL preferred sensor respectively. Each type sensor could sense FVN or FVL individually and standard curves for each analyte were generated. The signal intensity was linear with the concentration of each analyte in both FVN preferred and FVL preferred sensor. From sensing results with the mixture sample, the affinity of 1°Mab to FVN on the FVN-preferred sensor could not affect by the adding FVL molecules, and vice versa. Therefore, a mathematical model was provided to obtain the FV or FVL concentration simultaneously.

While various embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the following claims.

What is claimed is:

1. A method of diagnosing Factor V deficiency by determining a presence and quantity of Factor V Leiden (FVL) and Normal Factor V (FVN) in a sample from a subject comprising:

providing a first monoclonal antibody and a second monoclonal antibody, wherein the first monoclonal antibody was obtained against a peptide comprising FVN-20mer (SEQ ID NO 1): H-I-C-K-S-R-S-L-D-R-R-G-I-Q-R-A-

A-D-I-E-Q-NH₂ and specifically binds to native FVN as found in human plasma and wherein the binding affinity of the first antibody to native FVN is greater than the binding affinity of the first antibody to native FVL as found in human plasma of a person with FVL abnormality;

wherein the second monoclonal antibody was obtained against a peptide comprising FVL-20-mer (SEQ ID NO: 2): H-I-C-K-S-R-S-L-D-R-Q-G-I-Q-R-A-A-D-I-E-Q-NH₂ and specifically binds to native FVL as found in human plasma of a person with FVL abnormality and wherein the binding affinity of the second antibody to native FVL is greater than the binding affinity of the second antibody to native FVN;

immobilizing the first antibody and the second antibody on first and second optical sensing fibers, respectively;

exposing the sample to each of the immobilized antibodies separately to bind FVN and/or FVL in the sample to the optical sensing fibers;

probing the first and second sample-exposed optical sensing fibers with a fluorophore-tagged antibody that binds to both bound FVN and FVL with equal affinity;

obtaining fluorescent signal intensity values from bound fluorophore-tagged antibody for each of the first and second optical sensing fibers; and determining respective concentrations of FVN and FVL in the sample from said obtained signal intensity values, and determining if Factor V deficiency exists in the subject and/or severity of the deficiency in the subject from the determined concentrations of FVN and FVL in the sample.

2. The method of claim 1, wherein said determining concentrations comprises:

comparing said obtained signal values to a set of predetermined values indicative of FVN and FVL concentrations.

3. The method of claim 1, wherein said determining concentrations comprises:

entering the obtained signal values into a system of equations relating fluorescent signal intensities and concentrations, and solving the equations to determine unknown values associated with respective concentrations of FVN and FVL.

4. The method of claim 1, wherein said providing comprises creating and selecting the first and second monoclonal antibodies by a method comprising:

creating first and second antigenic peptides wherein the first antigenic peptide comprises FVN-20mer (SEQ ID NO 1): H-I-C-K-S-R-S-L-D-R-R-G-I-Q-R-A-A-D-I-E-Q-NH₂ and wherein the second antigenic peptide comprises FVL-20-mer (SEQ ID NO: 2): H-I-C-K-S-R-S-L-D-R-Q-G-I-Q-R-A-A-D-I-E-Q-NH₂;

obtaining the first and second antibodies against the first and second antigenic peptides, respectively, via hybridoma methods;

identifying respective affinities of the first and second antibodies for native FVN and native FVL; and selecting the first and second antibodies to provide based on said identified respective affinities.

5. A method of determining a presence and quantity of Factor V Leiden (FVL) and Normal Factor V (FVN) in a sample, the method comprising:

providing a first monoclonal antibody and a second monoclonal antibody, wherein the first monoclonal antibody was obtained against a peptide comprising FVN-20mer (SEQ ID NO 1): H-I-C-K-S-R-S-L-D-R-R-G-I-Q-R-A-A-D-I-E-Q-NH₂ and specifically binds to native FVN as found in human plasma, wherein binding affinity of the first antibody to native FVN is greater than the binding affinity of the first antibody to native FVL as found in human plasma of a person with FVL abnormality;

wherein the second monoclonal antibody was obtained against a peptide comprising FVL-20-mer (SEQ ID NO: 2): H-I-C-K-S-R-S-L-D-R-Q-G-I-Q-R-A-A-D-I-E-Q-NH₂ and specifically binds to native FVL as found in human plasma of a person with FVL abnormality and wherein the binding affinity of the second antibody to native FVL is greater than the binding affinity of the second antibody to native FVN;

immobilizing the first antibody and the second antibody on first and second optical sensing fibers, respectively;

exposing the sample to each of the immobilized antibodies separately to bind FVN and/or FVL in the sample to the optical sensing fibers;

probing the first and second sample-exposed optical sensing fibers with a fluorophore-tagged antibody that binds to both bound FVN and FVL with equal affinity;

obtaining fluorescent signal intensity values from bound fluorophore-tagged antibody for each of the first optical sensing fiber and the second optical sensing fiber; and solving a system of equations with the obtained signal intensity values to determine unknown values associated with respective concentrations of FVN and FVL in the sample, wherein the presence and respective quantities of FVN and FVL are determined according to the following system of equations:

$$SI_{TOTAL} \text{ for FVN preferable sensor } (SI_1) = A_1 \times C_{FVN} + B_1 \times C_{FVL}$$

$$SI_{TOTAL} \text{ for FVL preferable sensor } (SI_2) = A_2 \times C_{FVN} + B_2 \times C_{FVL}$$

where $SI_1$ represents signal intensity for the FVN preferable first optical fiber sensor, $SI_2$ represents signal intensity for the FVL preferable second optical fiber sensor, $A_1$ represents a slope of a standard curve showing a relationship between concentration and signal intensity of the FVN preferable sensor for FVN using samples with FVN only, $A_2$ represents a slope of a standard curve showing a relationship between concentration and signal intensity of the FVL preferable sensor for FVN using samples with FVN only, $B_1$ represents a slope of a standard curve showing a relationship between concentration and signal intensity for FVL using the samples with FVL only for the FVN preferable sensor, $B_2$ represents a slope of a standard curve showing a relationship between concentration and signal intensity for FVL using the samples with FVL only for the FVL preferable sensor, and C represents concentration to be determined.

6. The method of claim 5, wherein said providing the first and second antibodies comprises generating and selecting monoclonal antibodies by a method comprising:

creating first and second antigenic peptides wherein the first antigenic peptide comprises FVN-20mer (SEQ ID NO 1): H-I-C-K-S-R-S-L-D-R-R-G-I-Q-R-A-A-D-I-E-Q-NH₂ and wherein the second antigenic peptide comprises FVL-20-mer (SEQ ID NO: 2): H-I-C-K-S-R-S-L-D-R-Q-G-I-Q-R-A-A-D-I-E-Q-NH₂;

obtaining the first and second antibodies with the first and second antigenic peptides, respectively, via hybridoma methods;

identifying respective affinities of the first and second antibodies for native FVN and native FVL; and selecting the first and second antibodies to provide based on said identified respective affinities.

7. An immunological sensor for determining a presence and quantity of Factor V Leiden (FVL) and Normal Factor V (FVN) in a sample comprising:

a housing having a microfluidic network disposed therein;

first and second optical sensing fibers disposed within said microfluidic network and configured to be in fluid communication with one another, said first optical sensing fiber having a first monoclonal antibody immobilized thereon and a second optical sensing fiber having a second monoclonal antibody immobilized thereon, wherein the first monoclonal antibody was obtained against a peptide comprising FVN-20mer (SEQ ID NO 1): H-I-C-K-S-R-S-L-D-R-R-G-I-Q-R-A-A-D-I-E-Q-NH$_2$ and specifically binds to native FVN as found in human plasma and wherein the binding affinity of the first antibody to native FVN is greater than the binding affinity of the first antibody to native FVL as found in human plasma of a person with FVL abnormality;

wherein the second monoclonal antibody was obtained against a peptide comprising FVL-20-mer (SEQ ID NO: 2): H-I-C-K-S-R-S-L-D-R-Q-G-I-Q-R-A-A-D-I-E-Q-NH$_2$ and specifically binds to native FVL as found in human plasma of a person with FVL abnormality wherein the binding affinity of the second antibody to native FVL is greater than the binding affinity of the second antibody to native FVN;

an inlet for sample application to the microfluidic network and an outlet for discharging the sample following analysis, said inlet and said outlet configured to be in fluid communication with both said first and second optical sensing fibers and with one another; and a signal detector for detecting respective fluorescence signal emissions of said first and second optical sensing fibers following exposure of said first and second optical sensing fibers first to the sample and subsequently to a fluorophore-tagged antibody possessing equal affinity to both FVN and FVL when bound to the optical sensing fibers.

* * * * *

UNITED STATES PATENT AND TRADEMARK OFFICE
CERTIFICATE OF CORRECTION

PATENT NO.        : 9,140,707 B2                         Page 1 of 1
APPLICATION NO.   : 11/891452
DATED             : September 22, 2015
INVENTOR(S)       : Kyung Aih Kang et al.

It is certified that error appears in the above-identified patent and that said Letters Patent is hereby corrected as shown below:

In the Specification:

| | |
|---|---|
| Col. 4, line 11 | Please insert the word --a-- before "mutation". |
| Col. 6, line 22 | Please delete "determines" and insert --determining-- therefor. |
| Col. 10, line 55 | Please delete "verse" and insert --versa-- therefor. |
| Col. 11, line 24 | Please delete "same with" and insert --the same as-- therefor. |

Signed and Sealed this
Twenty-first Day of June, 2016

Michelle K. Lee
*Director of the United States Patent and Trademark Office*